United States Patent [19]

Voronkov et al.

[11] 4,010,210

[45] Mar. 1, 1977

[54] METHOD OF PREPARING AROMATIC AND HETEROCYCLIC SULPHIDES AND DISULPHIDES

[76] Inventors: Mikhail Grigorievich Voronkov, ulitsa Lermontova, 315, kv. 32; Eleonora Nikolaevna Deryagina, ulitsa Lermontova, 313a, kv. 79, both of Irkutsk; Evgeny Andreevich Chernyshev, Leninsky prospekt, 61/1, kv. 54; Valentina Ivanovna Savushkina, ulitsa Vavilova, 12, kv. 19, both of Moscow; Anatoly Samuilovich Nakhmanovich, Rossiiskaya ulitsa, 6, kv. 26, Irkutsk; Bella Moiseevna Tabenko, ulitsa Metallurgov, 48, korpus 5, kv. 49, Moscow, all of U.S.S.R.

[22] Filed: Apr. 29, 1975

[21] Appl. No.: 572,850

[52] U.S. Cl. .................. 260/609 D; 260/329 S
[51] Int. Cl.² .................................. C07C 149/00
[58] Field of Search ............... 260/329 S, 609 D

[56] References Cited

UNITED STATES PATENTS 2,490,257  12/1949  Crowley et al. .................. 260/609

OTHER PUBLICATIONS

Crowley, "Chem Abstracts" (1950), p. 4502(g).

*Primary Examiner*—James O. Thomas, Jr.
*Assistant Examiner*—A Siegel
*Attorney, Agent, or Firm*—Fleit & Jacobson

[57] ABSTRACT

The method of preparing sulphides and disulphides of aromatic and heteroaromatic series which involves reacting an aromatic or heteroaromatic chlorine- or bromine-derivative with hydrogen sulphide at a temperature of 150°–700° C with subsequent isolation of the end product.

5 Claims, No Drawings

METHOD OF PREPARING AROMATIC AND HETEROCYCLIC SULPHIDES AND DISULPHIDES

This invention relates to a method of preparing aromatic and heterocyclic sulphides and disulphides.

Aromatic and heteroaromatic sulphides and disulphides are widely used as additives to lubricating and fuel oils, pesticides, monomers, plasticizing agents, stabilizers, and intermediate products of organic synthesis.

Known in the prior art are methods for preparing aromatic and heterocyclic sulphides and disulphides. For example, a method for preparing diphenyl sulphide and its derivatives involves reacting the diazonium salt of chlorobenzene with sodium thiophenolate or reacting aryl halides with mercaptides of heavy metals. The method of preparing dithienyl sulphide involves reacting dithienyl disulphide with thiophenyl-lithium.

All the above-mentioned methods are labor-consuming and can only be carried out on a laboratory scale.

Known also are methods for preparing aromatic sulphides based on the reaction of aryl halides with hydrosulphide of alkali metal at high temperatures (200°–450° C) in a medium of polar organic compounds, for example, N-methyl-2-pyrrolidone, under excess or normal pressure.

Disadvantages inherent in the known methods are that they are effected in many stages, and the equipment required to carry out the process is complicated.

The aforesaid methods fail to be realized on a continuous principle. Another disadvantage of the known method is also the complexity of the process of isolation of the end product, which comprises the stages of extraction, drying, and regeneration of the solvent.

The object of this invention is to simplify the process of preparing aromatic and heterocyclic sulphides and disulphides and make it operate as a continuous process.

This object has been accomplished by providing a method for preparing sulphides and disulphides of aromatic and heteroaromatic series in which according to the invention, an aromatic or heteroaromatic chlorine- or bromine-derivative is reacted with hydrogen sulphide at a temperature of 150° – 700° C, with subsequent isolation of the end product.

If aromatic or heteroaromatic chlorine-derivative is used as the starting substance, it is recommended to carry out the process in the gaseous phase, in a counter-current or circulating system, at a temperature of 400° – 600° C.

If a bromine derivative of condensed aromatic compound is used as the starting material, the process should preferably be effected in the liquid phase at a temperature of 200°–300° C in a medium of an inert organic solvent.

It is recommended that O-dichlorobenzene, 1,2,4-trichlorobenzene, or decahydronaphthalene be used as the inert organic solvent.

Sulphides and disulphides of aromatic or heteroaromatic series are prepared by the interaction of heteroaryl halides with hydrogen sulphide at a temperature of 150°–700° C. The reaction proceeds as follows:

  (1)

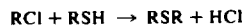  (2)

or, to summarize the two reactions

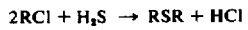  (3)

where R is aryl or heteroaryl. 400°–

The process can be carried out in a flow system with passing the vapours of aromatic or heteroaromatic chlorine derivative in a current of hydrogen sulphide at a temperature of 400–600° C through an empty silica tube. In this case the corresponding thiols are formed as side products according to reaction (1).

The reaction between hydrogen sulphide and aromatic or heteroaromatic chlorine derivatives should preferably be carried out in a recirculating system ensuring continuous return of the starting product and the intermediate thiol into the reaction zone (reaction (2) ).

The yield of the end product is 70–80 percent by weight. Diaryl disulphides are produced (12–20 percent by weight) by the reaction:

  (4)

The end product is isolated by rectification of the condensate in vacuum.

The reaction between bromine derivatives of condensed aromatic hydrocarbons and hydrogen sulphide is effected in the liquid phase, at a temperature of 200° – 300° C. As hydrogen sulphide is passed into a solution of, for example, 1-bromonaphthalene, 9-bromophenanthrene, or 9-bromoanthracene in a high-boiling inert solvent (O-dichlorobenzene, 1,2,4-trichlorobenzene, decahydronaphthalene etc), the corresponding aromatic sulphides are obtained, the yield being 60–70 percent by weight.

The end products are isolated by distillation in vacuum or by re-crystallization.

The proposed method has a number of advantages over the known methods. The process is effected in a single stage; the process can be run continuously, the equipment is simple (conventional flow system); the waste product of petroleum and coke industries, hydrogen sulphide, is used as one of the main reactants; the end product is isolated by a simple process consisting of vacuum distillation of the condensate, or re-crystallization of crystalline products; the process of recovery of solvent produces no effluents.

For a better understanding of the invention, the following examples of its practical embodiment are given by way of illustration.

Example 1. Chlorobenzene and hydrogene sulphide are passed through an empty silica tube (650 mm long, 30 mm in dia), heated to a temperature of 600° C, at a rate of 20 g (0.18 mole) and 5 litres per hour respectively. The process is continued for two hours. The condensate is collected in a receptacle cooled to a temperature of −10° C. As the condensate is distilled, 5.6 g (52 percent by weight for the reacted chlorobenzene) of diphenyl sulphide are isolated. Other products of the distillation process are 7.1 g of the starting chlorobenzene (conversion 65 percent by weight) and 4.5 g (38 percent by weight for the reacted chlorobenzene) of thiophenol.

Example 2. By a procedure similar to that described in Example 1, 6.1 g (46 percent by weight) of di(4-methylphenyl)sulphide, 6.6 g of the starting 4-chlorotoluene (conversion 70 percent by weight) and 6.7 g (45 percent by weight) of 4-thiocresol are obtained from 22 g (0.18 mole) of 4-chlorotoluene.

Example 3. Through a 570-mm long silica tube, 26 mm in diameter, heated to a temperature of 560° C, for 90 minutes are passed 40.0 g (0.34 mole) of 2-chlorothiophene and hydrogen sulphide at a rate of 5.2 litres per hour. The molar ratio of 2-chlorothiophene to hydrogen sulphide is 1:1. The condensate is distilled to give 16 g (48.2 percent by weight) of di(2-thienyl) sulphide boiling at 133°–140° C (5 mm Hg), $n_D^{20}$ = 1.6603, and 6.5 g of the starting 2-chlorothiophene (conversion 84 percent by weight).

Example 4. By a procedure similar to that described in Example 3, at a temperature of 550°–560° C and at a molar ratio of 2-chlorothiophene to hydrogen sulphide of 2:1, 50 g of di(2-thienyl) sulphide (58 percent by weight for the starting quantity and 85 percent by weight for the reacted chlorothiophene), 3 g of thiophene and 32 g of chlorothiophene (conversion 68 percent by weight) are obtained from 102 g (0.86 mole) of 2-chlorothiophene.

Example 5. By a procedure similar to that described in Exxample 3, at a temperature of 560° C and at a molar ratio of 2-chlorothiophene to hydrogen sulphide of 1:3, 10.5 g (32 percent by weight with respect to the starting quantity and 36.5 percent by weight for the reacted (2-chlorothiopehene) of di (2-thienyl)sulphide, 5 g of the starting 2-chlorothiophene (conversion 87 percent by weight) and 12 g (30 percent by weight for the starting quantity and 34.0 percent by weight for the reacted 2-chlorothiophene) of 2-thiophenthiol are obtained from 40.0 g (0.34 mole) of 2-chlorothiophene.

Example 6. By a procedure similar to that described in Example 3, at a temperature of 530° C, 18.0 g (40 percent by weight with respect to the starting quantity and 60 percent by weight for the reacted 2-methyl-5-chlorothiophene) of di(2-methyl-5-thienyl)sulphide boiling at 160°–170° C (5 mm Hg) and 16.5 g of the starting product (conversion 72 percent by weight), are obtained from 52 g (0.4 mole) of 2-methyl-5-chlorothiophene.

Example 7. By a procedure similar to that described in Example 3, at a temperature of 550° C, 31 g (33 percent by weight with respect to the starting quantity and 51 percent by weight for the reacted starting product) of di(5-methyl-2-thienyl)sulphide, 4 g of 2-methylthiophene, and 30 g of the starting 2-methyl-5-chlorothiophene (conversion 67.5 percent by weight) are obtained from 92 g (0.7 mole) of 2-methyl-3-chlorothiophene.

Example 8. By a procedure similar to that described in Example 3, at a temperature of 430° C, for three hours, 4.1 g (8.6 percent by weight) of di(thienyl)sulphide, 1.4 g (3.1 percent by weight) of 2,2-dithienyl disulphide and 1.38 g (3 percent by weight) of di(5-chloro-2-thienyl)sulphide boiling at 125°–127° C (0.08 mm Hg) and 44 g of unreacted 2,5-dichlorothiophene (conversion 51 percent by weight) are obtained from 90 g (0.6 mole) of 2,5-dichlorothiophene.

Example 9. By a procedure similar to that described in Example 3, at a temperature of 530° C, 17 g (23 percent by weight with reference to the starting quantity and 45 percent by weight for the reacted 2,5-dichlorothiophene) of di(5-chloro-2-thienyl) sulphide are obtained from 90 g (0.6 mole) of 2,5-dichlorothiophene.

Example 10. By a procedure similar to that described in Example 3, at a temperature of 480° C, from 2-chloro-5-bromothiophene and hydrogen sulphide taken in the molar ratio of 2:1 respectively, di(2-chloro-5-thienyl)sulphide is obtained in the quantity of 17 percent by weight with respect to the starting quantity and 30 percent by weight for the reacted 2-chloro-5-bromothiophene.

Example 11. A still of a re-circulating plant is loaded with 56.5 g (0.5 mole) of chlorobenzene. Its vapours, together with hydrogen sulphide current, are delivered at a rate of 2–3 litres per hour into an empty 400 mm-long silica tube having 30 mm in diameter, heated to a temperature of 600° C. The vapours are condensed and returned into the still.

In seven hours, the reaction products accumulated in the recirculating plant still are fractionated to isolate 21 g (77.8 percent by weight) of diphenyl sulphide, 4.1 g (13.9 percent by weight) of diphenyl disulphide melting at 59°–60° C, and 26.0 g of the starting chlorobenzene (conversion 54 percent by weight).

Example 12. By a procedure similar to that described in Example 11, at a temperature of 600° C, for four hours, 24.0 g (66.7 percent by weight) of di(4-methylphenyl)sulphide melting at 56.5° C, 13.1 g of unreacted 4-chlorotoluene (conversion 74.2 percent by weight) and 3.6 g (10 percent by weight) of 4-thiocresol are obtained from 50.01 g (0.4 mole) of 4-chlorotoluene.

Example 13. By a procedure similar to that described in Example 11, at a temperature of 500° C, for four hours, 11.2 g (70 percent by weight) of di(2-thienyl)-sulphide, 2.3 g (12.4 percent by weight) of di(thienyl)-disulphide, melting at 55°–56° C, and 10.8 g of unreacted 2-chlorothiophene (conversion 74 percent by weight) are obtained from 30.0 g (0.25 mole) of 2-chlorothiophene.

Example 14. Through a solution of 20.7 g (0.1 mole) of 1-bromonaphthalene in 12 ml of O-dichlorobenzene heated to a temperature of 205° C hydrogen sulphide is passed until hydrogen bromide stops evolving. The solvent is distilled in vacuum (at 5–10 mm Hg) and the remaining resinous mass is distilled in high vacuum (10$^{-2}$mm Hg). The resultant products are 2.5 g of unreacted 1-bromonaphthalene (conversion 81.9 percent by weight) and oil which crystallizes on standing. The yield after recrystallization from a mixture of alcohol and acetone is 5.8 g (40 percent by weight, for the unreacted 1-chloronaphthalene) of di(1-naphthyl) sulphide melting at 105°–107° C.

Example 15. By a procedure similar to that described in Example 14, hydrogen sulphide is passed into 20 g (0.1 mole) of molten 1-bromonaphthalene at a temperature of 220°–230° C for seven hours to obtain by distillation in vacuum (1 mm Hg) 7.5 g (52 percent by weight) of di(1-naphthyl)sulphide. The conversion is 82.5 percent by weight.

Example 16. Hydrogen sulphide is passed into a solution of 10.0 g (0.039 mole) of 9-bromophenanthrene in 20 ml of 1,2,4-trichlorobenzene heated to a temperature of 210° C for 28 hours. The solvent is distilled in vacuum of 10$^{-2}$ mm Hg to isolate 9.6 g of oil congealing in the cold. By recrystallization from a mixture of toluene and alcohol obtained are 4,4 g (56 percent by weight) of di(9-phenanthryl) sulphide. This is a white crystalline substance melting at 192°–193° C.

Found, in percent by weight: C, 86.68; H 4.76; S 8.39; mol.wt., 351. $C_{28}H_{18}S$.

Calculated, in percent by weight: C, 86.80; H, 4.66; S 8.30; mol. wt., 386.

Example 17. Hydrogen sulphide is passed into a solution of 20 g (0.08 mole) of 9-bromoanthracene in decahydronaphthalene at a temperature of 180° C for 14 hours, the solvent is separated by filtration, the residue is recrystallized from toluene to obtain 8.5 g (63.3 percent by weight) of di(9-anthryl) sulphide. This is a yellow crystalline substance melting at 257° C.

What is claimed is:

1. A method of preparing aryl sulphides and disulphides, comprising reacting a bromoaryl compound with hydrogen sulphide in the liquid phase at a temperature of about from 200° C. to 300° C. by bubbling the hydrogen sulphide through a solution of the bromine compound in a high boiling solvent which is inert with respect to the hydrogen solphide, and isolating the reaction product.

2. The method of claim 1 wherein the high boiling solvent is selected from the group consisting of o-dichlorobenzene, 1,2,4-trichlorobenzene, and decahydronaphthalene.

3. The method of claim 1 wherein the bromoaryl compound is 1-bromonaphthalene.

4. The method of claim 1 wherein the bromoaryl compound is 9-bromophenanthrene.

5. The method of claim 1 wherein the bromoaryl compound is 9-bromoanthracene.

* * * * *